(12) United States Patent
Aubert

(10) Patent No.: US 8,663,614 B2
(45) Date of Patent: Mar. 4, 2014

(54) METHOD OF SHAVING USING SALICYLIC ACID DERIVATIVES

(75) Inventor: Lionel Aubert, Asnieres sur Oise (FR)

(73) Assignee: L'Oreal, Paris (FR)

( * ) Notice: Subject to any disclaimer, the term of this patent is extended or adjusted under 35 U.S.C. 154(b) by 376 days.

(21) Appl. No.: 12/575,176

(22) Filed: Oct. 7, 2009

(65) Prior Publication Data
US 2010/0224204 A1 Sep. 9, 2010

Related U.S. Application Data

(60) Provisional application No. 61/105,946, filed on Oct. 16, 2008.

(30) Foreign Application Priority Data

Oct. 8, 2008 (FR) ...................................... 08 56811

(51) Int. Cl.
*A61K 8/365* (2006.01)
(52) U.S. Cl.
USPC ............................ 424/73; 132/202; 132/203
(58) Field of Classification Search
None
See application file for complete search history.

(56) References Cited

U.S. PATENT DOCUMENTS

| 4,767,750 | A | | 8/1988 | Jacquet et al. |
| 5,204,093 | A | * | 4/1993 | Victor .............................. 424/73 |
| 2004/0161392 | A1 | | 8/2004 | Hansenne et al. |

FOREIGN PATENT DOCUMENTS

| EP | 0 378 936 A2 | 7/1990 |
| FR | 2 581 542 A1 | 11/1986 |
| FR | 2 899 470 A1 | 10/2007 |

OTHER PUBLICATIONS

French Search Report of corresponding French Appln. No. 0856811 dated Aug. 14, 2009.

\* cited by examiner

*Primary Examiner* — Daniel Sullivan
*Assistant Examiner* — Barbara Frazier

(74) *Attorney, Agent, or Firm* — Novak Druce Connolly Bove + Quigg LLP

(57) ABSTRACT

The present invention relates to a method of shaving the skin, in particular the facial skin of men, using a composition comprising, in a cosmetically acceptable medium, at least one salicylic acid derivative of formula

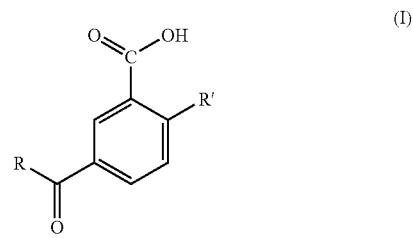

(I)

in which:
R represents a linear, branched or cyclic, saturated aliphatic chain containing from 3 to 11 carbon atoms; an unsaturated aliphatic chain containing from 3 to 17 carbon atoms bearing one or more conjugated or nonconjugated double bonds; an aromatic nucleus linked to the carbonyl radical directly or by means of saturated or unsaturated aliphatic chains containing from 2 to 7 carbon atoms; it being possible for said R groups to be substituted with one or more substituents, which may be identical or different, chosen from halogen atoms, a trifluoromethyl group, a hydroxyl group in free form or in a form esterified with an acid containing from 1 to 6 carbon atoms or else with a carboxyl function, which is free or esterified with a $C_1$-$C_6$ alcohol;
R' represents a hydroxyl group or an ester function of formula (II) below:

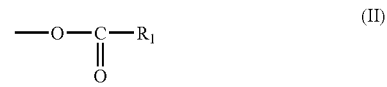

(II)

where $R_1$ represents a saturated or unsaturated, linear or branched aliphatic chain containing from 1 to 18 carbon atoms, and/or a salt thereof.
A subject of the present invention is also the use of at least one salicylic acid derivative of formula (I), in a cosmetic shaving composition, with the aim of facilitating the shaving of the hair.
A subject of the present invention is also the use of at least one salicylic acid derivative of formula (I), in a cosmetic shaving composition, with the aim of decreasing or even eliminating the ingrown hairs of the skin during shaving.

6 Claims, No Drawings

METHOD OF SHAVING USING SALICYLIC ACID DERIVATIVES

CROSS REFERENCE TO RELATED APPLICATIONS

This application claims priority to FR 0856811 filed Oct. 8, 2008 and claims benefit of U.S. Provisional Appl No. 61/105,946 filed Oct. 16, 2008, the entire contents of all are hereby incorporated by reference.

The present invention relates to a method of shaving the skin, in particular the facial skin of men, using a composition comprising, in a cosmetically acceptable medium, at least one salicylic acid derivative of formula (I) that will be defined below.

A subject of the present invention is also the use of at least one salicylic acid derivative of formula (I) that will be defined below, in a cosmetic shaving composition, with the aim of facilitating the shaving of the hair.

The beard of an adult man comprises on average from 8000 to 25 000 hairs. Shaving should be daily, in particular in the morning, since the beard grows approximately 0.4 mm in 24 hours. If the residues of a shave are analysed, 50% hairs and 50% dead cells are observed. The passing of the blade therefore has two simultaneous actions: cutting the hair and exfoliating the skin surface.

Now, shaving is traumatic for the skin and there exists a need to have cosmetic compositions capable of preparing the skin for shaving and also of facilitating said shaving.

The present invention aims specifically to offer a method of shaving which makes it possible to cause swelling of the hair, to reduce the firmness thereof so as to facilitate the passing of the blade, and to reduce the forces for bending the hair during shaving.

The present invention also aims to offer a method of shaving which enables a chemical exfoliation of the skin surface that will facilitate the shaving of the hair, since the skin will be freed of the dead cells obstructing the hair and making it more difficult to cut. Since the hair is thus exposed and the surface of the skin made more smooth, the blade of the razor will encounter less resistance and the risk of micro-cuts will be reduced. Another advantage of a method of shaving which enables chemical exfoliation of the skin surface is to be able to decrease the ingrown hairs. By removing the dead cells at the surface, the skin pores are freed gently, promoting growth of the hair. Ingrown hairs create considerable discomfort for shaving, especially for very curly beards which are more difficult to make neat.

It is known that certain salicylic acid derivatives in patent FR2581542 are known for their keratolytic and/or comedolytic properties, in particular in the treatment of acne. It is also known, in application WO2004/073745, that these same salicylic compounds also make it possible to reinforce the activity of cosmetic or dermatological active agents.

It is known, in U.S. Pat. No. 6,156,299, that acetylsalicylic acid combined with a specific mixture comprising propylene glycol, glycerol, isopropanol and, optionally, ethanol and/or water have been used in a skin treatment besides shaving for preventing or treating ingrown hairs.

The applicant has discovered, surprisingly, that, by using particular salicylic acid derivatives of formula (I) in a shaving composition for the skin, softening of the hair is obtained, making it possible to facilitate the shaving as the blade of the razor passes. Furthermore, the applicant has noted that these same salicylic compounds introduced into a shaving composition make it possible to obtain chemical exfoliation of the skin surface and therefore easy shaving, and also a decrease in or an elimination of the ingrown hairs.

This discovery forms the basis of the present invention.

The present invention relates to a method of shaving the skin, in particular the facial skin of men, comprising at least the following steps:

a) a composition comprising, in a cosmetically acceptable medium, at least one salicylic acid derivative of formula (I) that will be defined below is applied to the area of the skin to be shaved, b) the hairs are shaved by means of a razor.

Preferably, the area of skin thus treated is massaged for a period of time ranging from 20 seconds to 3 minutes, then the hairs are shaved, followed, after the shaving step, by rinsing with water.

The term "cosmetically acceptable medium" is intended to mean compatible with the skin and/or the skin appendages, which has a pleasant colour, odour and feel and which does not create unacceptable discomfort (stinging, tautness, redness) capable of discouraging the consumer from using this composition.

A subject of the present invention is also the use of at least one salicylic acid derivative of formula (I) that will be defined below, in a cosmetic shaving composition, with the aim of facilitating the shaving of the hair.

A subject of the present invention is also the use of at least one salicylic acid derivative of formula (I) that will be defined below, in a cosmetic shaving composition, with the aim of decreasing or even eliminating the ingrown hairs of the skin during shaving.

The salicylic acid derivatives of the invention correspond to formula (I) below:

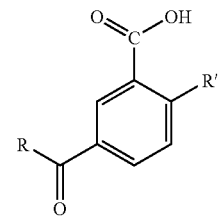

in which:

R represents a linear, branched or cyclic, saturated aliphatic chain containing from 3 to 11 carbon atoms; an unsaturated aliphatic chain containing from 3 to 17 carbon atoms bearing one or more conjugated or nonconjugated double bonds; an aromatic nucleus linked to the carbonyl radical directly or by means of saturated or unsaturated aliphatic chains containing from 2 to 7 carbon atoms; it being possible for said R groups to be substituted with one or more substituents, which may be identical or different, chosen from halogen atoms, a trifluoromethyl group, a hydroxyl group in free form or in a form esterified with an acid containing from 1 to 6 carbon atoms or else with a carboxyl function, which is free or esterified with a $C_1$-$C_6$ alcohol;

R' represents a hydroxyl group or an ester function of formula (II) below:

where $R_1$ represents a saturated or unsaturated, linear or branched aliphatic chain containing from 1 to 18 carbon atoms, and/or a salt thereof.

Among the preferred compounds of formula (I), mention may be made of those in which R represents a chain derived from linoleic acid, linolenic acid or oleic acid.

Another group of particularly advantageous compounds is those for which R denotes a $C_3$-$C_{11}$ linear alkyl bearing a free, esterified or salified carboxylic function, and R' denotes hydroxyl.

Among particularly preferred compounds of formula (I), use will be made of those in which R' denotes OH and R a $C_3$-$C_{11}$ linear alkyl group in particular chosen from 5-n-octanoylsalicylic acid (capryloylsalicylic acid), 5-n-decanoylsalicylic acid, 5-n-dodecanoylsalicylic acid and 5-n-heptyloxysalicylic acid, or salts thereof.

Among the salts of the compounds of formula (I), mention may be made of those obtained with an inorganic base, such as alkali-metal or ammonium hydroxides, sodium hydroxide, potassium hydroxide or aqueous ammonia; those obtained with an organic base, such as alkanolamines.

Use will more particularly be made of 5-n-octanoylsalicylic acid (or capryloylsalicylic acid) having the formula below:

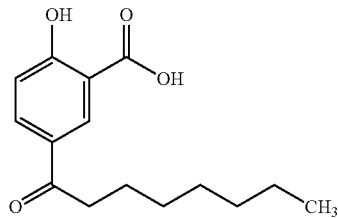 [SMILES: CCCCCCCC(=O)c1ccc(O)c(C(=O)O)c1]

such as the commercial product Mexoryl SAB manufactured by Chimex.

The salicylic acid derivatives of the invention of formula (I) are preferably present in the shaving compositions at contents ranging from 0.05% to 10%, in particular from 0.1% to 2%, and especially from 0.1% to 1% by weight, relative to the total weight of the composition.

The salicylic acid derivatives are known per se. They have been described in patent FR2581542, as have the processes for the synthesis thereof.

The shaving compositions according to the invention can be formulated in the form of simple aqueous solutions which can be applied to the face just before shaving. They contain, in general, other cosmetic or dermatological ingredients chosen, for example, from beard-wetting agents, skin-conditioning agents such as vitamins A, C and E, aloes, allantoin, panthenol, hydroxy acids, phospholipids, triglycerides, plant oils, amino acids, cleansing agents, foaming agents, emollients, hydrating agents (glycerol, sorbitol, propylene glycol), surfactants (for example, soaps, non-ionic, anionic or amphoteric surfactants), thickeners or gelling agents, propellants, self-foaming agents, fragrances, colouring agents, antioxidants and preservatives.

According to one particular embodiment of the invention, the shaving compositions may be in the form of a lotion, a cream, a foam or a gel. Such compositions preferably comprise at least from 60% to 95% of water, more preferably from 70% to 90% of water, relative to the total weight of the composition, and from 3% to 25% by weight of at least one surfactant chosen from anionic, non-ionic, amphoteric or zwitterionic surfactants, or mixtures thereof, and more preferably from 5% to 20% by weight.

Among the anionic surfactants that can be used for the invention, mention may be made of soaps which are, for example, the sodium, potassium or alkanolamine (triethanolamine) salts of $C_{10}$-$C_{20}$, and preferably $C_{12}$-$C_{18}$, fatty acid. Among the soaps, mention may be made of lauric acid, oleic acid, coconut oil acid, myristic acid, palmitic acid, stearic acid or mixtures thereof.

Among the anionic surfactants that can be used for the invention, mentioned may be made of the sodium, potassium or alkanolamine (triethanolamine) salts of N-acylsarcosine comprising a fatty chain in which the acyl group is $C_{10}$-$C_{20}$, and preferably $C_{12}$-$C_{20}$, for instance the stearoyl sarcosine, myristoyl sarcosine, palmitoyl sarcosine, oleoyl sarcosine, lauroyl sarcosine and cocoyl sarcosine salts and mixtures thereof. Even more preferably, they are chosen from stearoyl sarcosine, myristoyl sarcosine and mixtures thereof. The sarcosine(s) is (are) present at contents ranging from 2% to 15% by weight, and preferably ranging from 4% to 10%, relative to the total weight of the composition. The N-acylsarcosine derivatives can be used in preneutralized form, or in the form of a free acid which is neutralized with a base such as sodium hydroxide, potassium hydroxide or alkanolamine. A sufficient amount of base should be used to neutralize the sarcosine in the aqueous phase and to produce a pH of from 4 to 8.5, and more preferably from 5 to 7. To achieve this pH range, the sarcosine is preferably 60% to 80% neutralized. The sarcosine will preferably be used in slight molar excess relative to the base. The base is preferably present at a content ranging from 1% to 6% relative to the total weight of the composition.

Among the anionic surfactants that can be used for the invention, mention may also be made of carboxylates, alkyl sulphates which may or may not be oxyethylenated, sulphonates, alkyl sulphoacetates, phosphates, polypeptides, anionic derivatives of alkyl polyglucoside, and mixtures thereof.

As carboxylates, mention may, for example, be made of:
amido ether carboxylates (AECs), such as sodium lauryl amido ether carboxylate (3 EO) sold under the name Akypo Foam 30® by the company Kao Chemicals;
polyoxyethylenated carboxylic acid salts, such as oxyethylenated (6 EO) sodium lauryl ether carboxylate (65/25/ 10 $C_{12\text{-}14\text{-}16}$) sold under the name Akypo Soft 45 NV® by the company Kao Chemicals; polyoxyethylenated and carboxymethylated fatty acids of olive oil, the product sold under the name Olivem 400® by the company Biologia E Tecnologia; oxyethylenated (6 EO) sodium tridecyl ether carboxylate sold under the name Nikkol ECTD-6NEX® by the company Nikkol;
acetates, such as sodium 2-(2-hydroxyalkyloxy)acetate sold under the name Beaulight Shaa by the company Sanyo;
alaninates such as sodium N-lauroyl-N-methylamidopropionate, sold under the name Sodium Nikkol Alaninate LN 30® by the company Nikkol or under the name Alanone ALE® by the company Kawaken, and triethanolamine N-lauroyl-N-methylalanine sold under the name Alanone Alta® by the company Kawaken; (3) acylglutamates, such as triethanolamine monococoylglutamate sold under the name Acylglutamate CT-12® by the company Ajinomoto, and triethanolamine lauroylglutamate sold under the name Acylglutamate LT-12® by the company Ajinomoto; (4) aspartates, such as the mixture of triethanolamine N-lauroylaspartate and triethanolamine N-myristoylaspartate, sold under the name Asparack® by the company Mitsubishi; (5) glycinates, such as sodium N-cocoylglycinate sold under the names Amilite GCS-12® and Amilite GCK 12 by the company Ajinomoto;

citrates, such as the oxyethylenated (9 EO) citric monoester of coco alcohols sold under the name Witconol EC 1129 by the company Goldschmidt; and galacturonates, such as sodium dodecyl-D-galactoside uronate sold by the company Soliance.

As oxyethylenated or non-oxyethylenated alkyl sulphates, mention may be made, for example, of (2.2 EO) sodium lauryl ether sulphate (70/30 $C_{12-14}$) sold under the name Sipon AOS 225® by the company Cognis, (3 EO) ammonium lauryl ether sulphate (70/30 $C_{12-14}$) sold under the name Sipon LEA 370® by the company Cognis, (9 EO) ammonium alkyl ($C_{12}$-$C_{14}$) ether sulphate sold under the name Rhodapex AB/20® by the company Rhodia Chimie, and the mixture of sodium and magnesium lauryl and oleyl ether sulphate sold under the name Empicol BSD 52 by the company Albright & Wilson.

As sulphonates, mention may be made, for example, of (1) α-olefin sulphonates, such as sodium α-olefin ($C_{14-16}$) sulphonate sold under the name Bioterge AS-40® by the company Stepan, under the names Witconate AOS Protege® and Sulframine AOS PH 12® by the company Witco, the sodium secondary olefin sulphonate sold under the name Hostapur SAS 30® by the company Clariant;

(2) isethionates, such as sodium cocoylisethionate, such as the product sold under the name Jordapon CI P® by the company Jordan; and (3) taurates, such as the sodium salt of palm kernel oil methyltaurate sold under the name Hostapon CT PATE® by the company Clariant; N-acyl N-methyltaurates, such as sodium N-cocoyl N-methyltaurate sold under the name Hostapon LT-SF® by the company Clariant or sold under the name Nikkol CMT-30-T® by the company Nikkol, sodium palmitoyl methyltaurate sold under the name Nikkol PMT® by the company Nikkol.

As sulphosuccinates, mention may be made, for example, of oxyethylenated (3 EO) lauryl alcohol monosulphosuccinate (70/30 $C_{12}/C_{14}$) sold under the names Setacin 103 Special®, Rewopol SB-FA 30 K 4® by the company Witco, the disodium salt of a $C_{12}$-$C_{14}$ alcohol hemisulphosuccinate sold under the name Setacin F Special Paste® by the company Zschimmer Schwarz, oxyethylenated (2 EO) disodium oleamidosulphosuccinate sold under the name Standapol SH 135® by the company Cognis, oxyethylenated (5 EO) laurylamide monosulphosuccinate sold under the name Lebon A-5000® by the company Sanyo.

As phosphates, mention may be made, for example, of monoalkyl phosphates and dialkyl phosphates, such as lauryl monophosphate sold under the name Map 20® by the company Kao Chemicals, the potassium salt of dodecylphosphoric acid, as a mixture of monoester and diester (mainly diester) sold under the name Crafol AP-31® by the company Cognis, the mixture of octylphosphoric acid monoester and diester sold under the name Crafol AP-20® by the company Cognis, and the mixture of ethoxylated (7 mol of EO) 2-butyloctanol phosphoric acid monoester and diester sold under the name Isofol 12 7 EO-Phosphate Ester® by the company Condea.

As polypeptides (which are compounds obtained by condensation of a fatty chain over cereal, and especially wheat and oat, amino acids), mention may be made, for example, of the potassium salt of hydrolysed lauroyl wheat protein, sold under the name Aminofoam W OR® by the company Croda; the triethanolamine salt of hydrolysed cocoyl soya bean protein, sold under the name May-Tein SY® by the company Maybrook; the sodium salt of lauroyl oat amino acids, sold under the name Proteol Oat® by the company Seppic; the hydrolysate of collagen grafted onto coconut fatty acid sold under the name Geliderm 3000® by the company Deutsche Gelatine; and soya bean proteins acylated with hydrogenated coconut acids, sold under the name Proteol VS 22® by the company Seppic.

As anionic alkyl polyglucoside derivatives, mention may especially be made of glyceryl citrates, tartrates, sulphosuccinates, carbonates and ethers obtained from alkyl polyglucosides. Mention may be made, for example, of the sodium salt of cocoyl polyglucoside (1.4) tartaric ester, sold under the name Eucarol AGE-ET® by the company Cesalpinia; the disodium salt of cocoyl polyglucoside (1.4) sulphosuccinic ester, sold under the name Essai 512 MP® by the company Seppic; the sodium salt of cocoyl polyglucoside (1.4) citric ester, sold under the name Eucarol AGE-EC® by the company Cesalpinia, and the sodium lauryl polyglucoside ether carboxylate sold under the name Plantapon LGC SORB by the company Cognis.

Preferably, the salts of $C_6$-$C_{24}$ alkyl ether sulphates having 1 to 30 ethylene oxide groups will be used, in particular the alkali metal or alkaline-earth metal, ammonium, amine or amino alcohol salts and more particularly the sodium salts and even more particularly oxyethylenated sodium ($C_{12}$-$C_{14}$) alkyl ether sulphates having an average number of ethylene oxide groups between 1 and 4, and more particularly sodium laureth sulphate (CTFA name).

The amphoteric and zwitterionic surfactants in accordance with the invention may be chosen from alkylbetaines, N-alkylamidobetaines and derivatives thereof, sultaines, alkylpolyaminocarboxylates (APACs) and alkylamphoacetates, and mixtures thereof.

As alkylbetaines, mention may, for example, be made of cocobetaine, for instance the product sold under the name Dehyton AB-30® by the company Cognis or the commercial products Mirataine BB/FLA from Rhodia or Empigen BB/FL from Huntsman; laurylbetaine, for instance the product sold under the name Genagen KB® by the company Clariant or the product sold under the name Empigen BB/LS® by the company Huntsman; oxyethylenated (10 EO) laurylbetaine, for instance the product sold under the name Lauryl Ether (10 EO) Betaine® by the company Shin Nihon Rica; oxyethylenated (10 EO) stearylbetaine, for instance the product sold under the name Stearyl Ether (10 EO) Betaine® by the company Shin Nihon Rica.

Among the N-alkylamidobetaines and derivatives thereof, mention may, for example, be made of the cocamidopropylbetaine sold under the name Lebon 2000 HG® by the company Sanyo or under the name Empigen BB® by the company Albright & Wilson; the lauramidopropylbetaine sold under the name Rewoteric AMB12P® by the company Witco.

As sultaines, mention may be made of the cocoylamidopropylhydroxysulphobetaine sold under the name Crosultaine C-50® by the company Croda.

As alkylpolyaminocarboxylates (APACs), mention may be made of the sodium cocoylpolyaminocarboxylate sold under the name Ampholak 7 CX/C® and Ampholak 7 CX® by the company Akzo Nobel; the sodium stearylpolyamidocarboxylate sold under the name Ampholak 7 TX/C® by the company Akzo Nobel; the sodium carboxymethyloleylpolypropylamine sold under the name Ampholak XO7/C® by the company Akzo Nobel.

As alkylamphoacetates, mention may, for example, be made of N-disodium N-cocoyl-N-carboxymethoxyethyl-N-carboxymethylethylenediamine (CTFA name: disodium cocamphodiacetate), for instance the product sold under the name Miranol C2M Concentrate NP® by the company Rhodia Chimie; and N-sodium N-cocoyl-N-hydroxyethyl-N-carboxymethylethylenediamine (CTFA name: sodium cocamphoacetate).

Among the amphoteric or zwitterionic surfactants, use will more particularly be made of alkylbetaines, and even more preferably laurylbetaine, and more particularly laurylbetaine in the form of an aqueous solution at 30% as a mixture with sodium chloride (INCI name: laurylbetaine (and) sodium chloride), such as the commercial product Empigen BB/LS from Huntsman.

The compositions according to the invention comprise one or more non-ionic surfactants. These are compounds that are well known per se (in this respect see, in particular, "Handbook of Surfactants" by M. R. Porter, published by Blackie & Son (Glasgow and London), 1991, pp. 116-178). Thus they can especially be chosen from fatty alcohols having a fatty chain that preferably comprises 8 to 20 carbon atoms; polyethoxylated, polypropoxylated or polyglycerolated alcohols, α-diols, alkylphenols or fatty acids, having a fatty chain comprising, preferably, 8 to 20 carbon atoms, and where the number of ethylene oxide groups or propylene oxide groups varies preferably from 2 to 60 and the number of glycerol groups possibly ranging especially from 2 to 30. Mention may also be made of the copolymers of ethylene and propylene oxide, the condensates of ethylene and propylene oxide with fatty alcohols; polyethoxylated fatty amides preferably having from 2 to 30 mol of ethylene oxide, polyglycerolated fatty amides preferably comprising, on average, 1 to 5, and in particular 1.5 to 4, glycerol groups; polyethoxylated fatty amines preferably having 2 to 30 mol of ethylene oxide; ethoxylated sorbitan fatty acid esters preferably having 2 to 30 mol of ethylene oxide; sucrose fatty acid esters, polyethylene glycol fatty acid esters, ($C_6$-$C_{24}$)alkyl polyglycosides, N—($C_6$-$C_{24}$)alkylglucamine derivatives, amine oxides such as ($C_{10}$-$C_{14}$) alkylamine oxides or N—($C_{10}$-$C_{14}$) acylaminopropylmorpholine oxides; and mixtures thereof.

As alkyl polyglucosides, preferably those having an alkyl group comprising 6 to 30 carbon atoms and preferably 8 to 16 carbon atoms, and having a hydrophilic group (glucoside) preferably comprising 1.2 to 3 saccharide units are used. As alkyl polyglucosides, mention may be made, for example, of decyl glucoside ($C_9$/$C_{11}$ alkyl polyglucoside (1.4)) such as the product sold under the name Mydol 10® by the company Kao Chemicals, under the name Plantaren 2000 UP® by the company Cognis, and under the name Oramix NS 10® by the company Seppic; caprylyl/capryl glucoside, such as the product sold under the name Oramix CG 110® by the company Seppic; lauryl glucoside, such as the products sold under the names Plantaren 1200 N® and Plantacare 1200® by the company Cognis; and coco glucoside, such as the product sold under the name Plantacare 818/UP® by the company Cognis.

The maltose derivatives are, for example, those described in document EP-A-566 438, such as O-octanoyl-6'-D-maltose, or else O-dodecanoyl-6'-D-maltose described in document FR-2 739 556.

Among the polyglycerolated fatty alcohols, mention may be made of polyglycerolated (3.5 mol of glycerol) dodecanediol, a product manufactured under the name Chimexane NF® by the company Chimex.

The preferred non-ionic surfactants are chosen from:
fatty alcohols having a $C_8$-$C_{20}$ fatty chain, more preferentially having a $C_{12}$-$C_{18}$ fatty chain, such as for example myristyl alcohol, lauryl alcohol, stearyl alcohol and octyldodecanol;

polyoxyethylenated ethers of fatty alcohols having a $C_8$-$C_{20}$ fatty chain, more preferentially having a $C_{12}$-$C_{18}$ fatty chain and having 2 to 60, more preferentially 2 to 30 ethylene oxide units. Among these compounds, mention may be made, for example, of Oleth-20, Steareth-21, Ceteth-20, Laureth-4 and Laureth-23.

The compositions of the invention may also contain a gelling agent and, for example, contain at least one non-volatile liquid hydrocarbon. The terms "volatile" and "liquid" signify that these materials are liquid at ambient temperature and have a boiling point above 200° C. Among these liquid hydrocarbons, mention may be made of mineral oils and branched aliphatic liquids. These liquids preferably have from 16 to 48 carbon atoms, more preferentially from 20 to 40 carbon atoms, and a kinetic viscosity (measured according to the ASTM D445 standard) of 5 to 100 cst, and more preferentially of 10 to 70 cst at 40° C. The preferred non-volatile liquid hydrocarbons are chosen from mineral oils having a kinetic viscosity of 10 to 70 cst, hydrogenated polyisobutenes having a molecular weight of from 320 to 420, and mixtures thereof. The non-volatile liquid hydrocarbon(s) is (are) preferably present at concentrations of less than or equal to 10%, and preferably less than or equal to 7% by weight, relative to the total weight of the composition.

The compositions of the invention may also contain a water-soluble gelling agent or a thickener to improve the consistency and the stability of the gel or to adjust the viscosity.

Among these auxiliary gelling agents, mention may be made of hydroxyalkylcellulose polymers such as hydroxyethylcellulose or hydroxypropylcellulose (products sold, respectively, under the trade name Natrosol or Klucel); acrylic acid/polyallyl sucrose copolymers (products sold under the trade name Carbopol); carboxymethylcellulose and cellulose methyl ether (products sold under the trade name Methocel); natural or synthetic gums, or starches. The gelling agents or thickeners are preferably present at concentrations ranging from 0.01% to 5% by weight, more preferably from 0.05% to 2% by weight, and even more preferably from 0.01% to 2% by weight relative to the total weight of the composition.

The compositions according to the invention may also contain a variety of conventional cosmetic ingredients for improving the aesthetic qualities and the effectiveness of these compositions.

The compositions according to the invention may also contain, in addition, a conditioning cationic polymer for improving the lubricity and feel of the skin after shaving. Mention may, for example, be made of the quaternary ammonium salts of hydroxyethylcellulose, such as polyquaternium-10 or polyquaternium-24.

Mention may also be made of the following cationic polymers:
Polyquaternium 5, such as the product Merquat 5 sold by the company Calgon;
Polyquaternium 6, such as the product Salcare SC 30 sold by the company Ciba, and the product Merquat 100 sold by the company Calgon;
Polyquaternium 7, such as the products Merquat S, Merquat 2200 and Merquat 550 sold by the company Calgon, and the product Salcare SC 10 sold by the company Ciba;
Polyquaternium 11, such as the products Gafquat 755, Gafquat 755N and Gafquat 734 sold by the company ISP;
Polyquaternium 15, such as the product Rohagit KF 720 F sold by the company Rohm;

Polyquaternium 16, such as the products Luviquat FC905, Luviquat FC370, Luviquat HM552 and Luviquat FC550 sold by the company BASF;

Polyquaternium 22, such as the product Merquat 280 sold by the company Calgon;

Polyquaternium 28, such as the product Styleze CC10 sold by the company ISP;

Polyquaternium 39, such as the product Merquat PLUS 3330 sold by the company Calgon;

Polyquaternium 44, such as the product Luviquat Care sold by the company BASF;

Polyquaternium 46, such as the product Luviquat Hold sold by the company BASF; and Polyquaternium 47, such as the product Merquat 2001 sold by the company Calgon.

It is also possible to use, as the cationic polymer, cationic guars such as the product Jaguar sold by the company Rhodia.

The cationic conditioning polymer or polymers is (are) preferably present at concentrations ranging from 0.05% to 2% by weight, more preferentially ranging from 0.1% to 1% by weight, relative to the total weight of the composition.

Other additives may also be used in the compositions of the invention, such as:

humectants such as sorbitol;

emollients such as fatty esters, for instance isopropyl myristate, decyl oleate, 2-ethyhexyl palmitate, PEG-7 glyceryl cocoate and glyceryl linoleate; propoxylated fatty ethers such as PPG-10 cetyl ether and PPG-11 stearyl ether; diglycerides or triglycerides such as lecithin, the mixture of capric/caprylic triglycerides, PEG-10 soy sterol or vegetable oils;

refreshing agents and soothing agents such as menthol, aloe, allantoin, lanolin, bisabolol or hyaluronic acid;

lubricants such as polyethylene glycols (i.e. PEG-14M, PEG-23M), fluorosurfactants, silicones (i.e. dimethicone, dimethiconol, dimethicone copolyol, stearyl dimethicone, cetyl dimethicone copolyol, cyclomethicone, etc.);

vitamins, including precursors and derivatives such as panthenol, tocopheryl acetate, niacinamide, retinyl palmitate or vitamin A palmitate;

colorants;

fragrances;

antioxidants;

antibacterial and/or antifungal agents;

preservatives (i.e. methylchloroisothiazolinone, methylisothiazolinone, DMDM hydantoin, iodopropynyl butylcarbamate);

fillers.

Among the fillers that can be used according to the invention, mention may be made of organic powders. In the present application, the term "organic powder" is intended to mean any solid insoluble in the medium at ambient temperature (25° C.).

As organic powders that may be used in the composition of the invention, mention may, for example, be made of polyamide particles and especially those sold under the name Orgasol by the company Atochem; polyethylene powders; microspheres based on acrylic copolymers, such as those made of ethylene glycol dimethacrylate/lauryl methacrylate copolymer, sold by the company Dow Corning under the name Polytrap; polymethyl methacrylate microspheres, sold under the name microsphere M-100 by the company Matsumoto or under the name Covabead LH85 by the company Wackherr; ethylene-acrylate copolymer powders, for instance those sold under the name Flobeads by the company Sumitomo Seika Chemicals; expanded powders such as hollow microspheres and especially microspheres formed from a terpolymer of vinylidene chloride, of acrylonitrile and of methacrylate and sold under the name Expancel by the company Kemanord Plast under the references 551 DE 12 (particle size of approximately 12 μm and density of 40 kg/m$^3$), 551 DE 20 (particle size of approximately 30 μm and density of 65 kg/m$^3$), 551 DE 50 (particle size of approximately 40 μm), or the microspheres sold under the name Micropearl F 80 ED by the company Matsumoto; powders of natural organic materials such as starch powders, especially of maize starch, wheat starch or rice starch, which may or may not be crosslinked, such as the powders of starch crosslinked with octenylsuccinate anhydride, sold under the name Dry-Flo by the company National Starch; silicone resin microbeads such as those sold under the name Tospearl by the company Toshiba Silicone, in particular Tospearl 240; amino acid powders such as the lauroyllysine powder sold under the name Amihope LL-11 by the company Ajinomoto; particles of wax microdispersion, which preferably have mean sizes of less than 1 μm and in particular ranging from 0.02 μm to 1 μm, and which are essentially constituted of a wax or a mixture of waxes, such as the products sold under the name Aquacer by the company Byk Cera, and in particular: Aquacer 520 (mixture of synthetic and natural waxes), Aquacer 514 or 513 (polyethylene wax), Aquacer 511 (polymeric wax), or such as the products sold under the name Jonwax 120 by the company Johnson Polymer (mixture of polyethylene wax and paraffin wax) and under the name Ceraflour 961 by the company Byk Cera (micronized modified polyethylene wax); and mixtures thereof.

Of course, those skilled in the art will take care to select the optional additional compound(s) mentioned above and/or the amounts thereof in such a way that the advantageous properties intrinsically associated with the compositions in accordance with the invention are not, or are not substantially, adversely affected by the envisaged addition(s).

According to one particular embodiment of the invention, the shaving compositions may be in the form of a shaving foam. The shaving foams are, in general, in the form of an oil-in-water emulsion in which the aqueous phase contains, in general, a water-soluble anionic surfactant. The product is generally packaged in a monoblock aerosol container in which the propellant is in a mixture with the fluid; the foam forms at the outlet of the aerosol device.

The propellant is preferably chosen from volatile hydrocarbons and halogenated volatile hydrocarbons. The boiling point of the propellant preferably ranges from −20 to 40° C. The propellants that can be used according to the invention are chosen from $C_4$-$C_6$ aliphatic hydrocarbons such as n-pentane, isopentane, neopentane, n-butane or isobutane, and mixtures thereof. More preferably, an isopentane/butane/propane mixture will be used. The propellant is preferably present at concentrations ranging from 1% to 10% by weight, and more preferably from 2% to 6% by weight, relative to the total weight of the composition.

According to one particular embodiment of the invention, the shaving compositions may be in the form of a self-foaming gel. Such formulations are in the form of an oil-in-water emulsion in which the self-foaming agent, generally a volatile aliphatic hydrocarbon (i.e. a hydrocarbon of low boiling point), is solubilized in the oily phase, and the aqueous phase generally comprises a water-soluble anionic surfactant. The product is generally packaged in an aerosol container with a separation such as a piston or a flexible bag to separate the self-foaming agent from the propellant required to expel the product. The device may also be a flexible tube; a pump-dispenser bottle or a bottle with a deformable wall. The product is applied in the form of a transparent, translucent or opaque gel that is substantially free of foam until spread onto the skin, at which moment the foam is produced by evaporation of the volatile hydrocarbon foaming agent.

The self-foaming agent is preferably chosen from volatile hydrocarbons and halogenated volatile hydrocarbons having a boiling point sufficiently low to allow the latter to evaporate and to foam the gel upon application to the skin, and a boiling point sufficiently high to avoid producing a foam prematurely. The boiling point of the self-foaming agent preferably ranges from −20 to 40° C. The self-foaming agent is preferably chosen so as to form a vapour pressure at 20° C. of 3 to 20 psig, and preferably 5 to 15 psig. The self-foaming agents that can be used according to the invention are chosen from $C_4$-$C_6$ aliphatic hydrocarbons such as n-pentane, isopentane, neopentane, n-butane or isobutane, and mixtures thereof. More preferably, a mixture of isopentane/isobutane in a ratio by weight ranging from 1/1 to 3/1 will be used. The self-foaming agent is preferably present at concentrations ranging from 1% to 8% by weight, and more preferably from 2% to 5% by weight, relative to the total weight of the composition.

The invention also relates to a shaving kit, characterized in that it comprises:
(a) at least one shaving composition as defined above and
(b) at least one razor, in particular a disposable razor, and optionally
(c) a means for spreading a shaving composition.

According to one particular embodiment of the invention, the kit may also contain an aftershave composition to soothe razor burn.

The examples which follow serve to illustrate the invention. The amounts indicated are in % by weight relative to the total weight of the composition, and the names of the compounds are given as chemical names or INCI names, as appropriate.

EXAMPLES 1 and 2

Shaving Foam Fluid

| Ingredients | Ex 1(*) | Ex 2 |
|---|---|---|
| Stearic acid | 5.16 | 5.16 |
| Palmitic acid | 4.30 | 4.30 |
| Myristic acid | 0.29 | 0.29 |
| Glycerol | 3 | 3 |
| Capryloylsalicylic acid | — | 0.3 |
| Hydroxypropylcellulose (Klucel MF from Aqualon) | 0.10 | 0.10 |
| Triethanolamine | 5 | 5 |
| Steareth-2 | 1.50 | 1.50 |
| Steareth-20 | 1.50 | 1.50 |
| Caprylic/capric triglyceride | 2 | 2 |
| Fragrance | 1 | 1 |
| Preservatives | qs | qs |
| Deionized water | qs 100 | qs 100 |
| % Decrease in rigidity of the hair | 13.6% | 25% |

(*)not part of the invention

A comparative test is carried out between these two shaving foam fluids, the objective of which is to show their influence on the swelling of the hair and the softening of said hair when it is immersed in a shaving composition after having been immersed beforehand in water. The force for bending the fibre thus immersed is measured.

Samples of hair are inserted into plastic test-sample plaques of the fibre tip type comprising a free end. The length of the free hair sample undergoing the test is 5 mm. The hair is oriented in the root-end direction.

The samples will be immersed for 10 minutes in water and then for 10 minutes in the shaving composition 1 or 2.

The force for bending the hair treated or not treated with the shaving product is measured, after immersion, by means of a Diastron FBS 900 device which records the force required to bend the fibre. This device is equipped with a rotary cylinder. It enables measurements on various axes of the hair so as to take into account its ellipticity. On the basis of the force measured and then standardized with respect to the dimensions of the sample, the stress is calculated and the flexural modulus is determined.

The parameters used with this device are
minimum detection force: 2 mg
speed of movement: 0.05 mm/s
maximum vertical movement: 0.4 mm
angle: 0°
cylinder/test-sample distance: 2 mm
acquisition rate: 10 Hz The amount of decrease in rigidity of the hair treated with the shaving composition, compared with that measured with the nontreated hair (immersed in water), is then calculated. It is observed that composition 2 according to the invention, comprising capryloylsalicylic acid, makes it possible to further soften the hair, and therefore to improve shaving, compared with composition 1 which does not comprise any salicylic derivative.

The invention claimed is:
1. A method of shaving hair comprising:
a) applying a shaving composition to an area to be shaved, wherein the shaving composition comprises an amount of 5-n-octanoysalicyclic acid in the range of 0.1% to 1% by weight, based on the total weight of the shaving composition, and is sufficient to decrease the rigidity of hair;
b) decreasing the rigidity of the hair; and
c) shaving the hair with a razor.
2. The method according to claim 1, in which the area to be shaved is massaged for a period of time ranging from 20 seconds to 3 minutes, then the hairs are shaved, followed by rinsing with water.
3. The method according to claim 1, wherein the shaving composition is in the form of a lotion, a cream, a gel, a foam or a self-foaming gel.
4. The method according to claim 2, wherein the shaving composition is in the form of a lotion, a cream, a gel, a foam or a self-foaming gel.
5. The method according to claim 1, wherein the method is applied to the face of a man.
6. The method of claim 1, the shaving composition comprises an amount of 5-n-octanoysalicyclic acid in the range of 0.3% to 1% by weight, based on the total weight of the shaving composition, that is sufficient to decrease the rigidity of hair.

* * * * *